United States Patent [19]

Mullett

[11] Patent Number: 5,031,618
[45] Date of Patent: Jul. 16, 1991

[54] POSITION-RESPONSIVE NEURO STIMULATOR

[75] Inventor: Keith R. Mullett, Minneapolis, Minn.
[73] Assignee: Medtronic, Inc., Minneapolis, Minn.
[21] Appl. No.: 490,065
[22] Filed: Mar. 7, 1990
[51] Int. Cl.$^5$ .............................................. A61N 1/05
[52] U.S. Cl. ................................... 128/421; 128/784
[58] Field of Search .................. 128/419 R, 421, 422, 128/423, 783, 784

[56] References Cited

U.S. PATENT DOCUMENTS

| | | | |
|---|---|---|---|
| 4,044,774 | 8/1977 | Corbin et al. | 128/419 R |
| 4,141,365 | 2/1979 | Fischell et al. | 128/419 R |
| 4,538,624 | 9/1985 | Tarjan | 128/419 R |
| 4,846,195 | 7/1989 | Alt | 128/782 |

OTHER PUBLICATIONS

Electrical Stimulation of the Spinal Cord, The Phenomenon of Changing Paresthesias, by G. H. Spincemaille and C. H. A. Wittens.

Primary Examiner—Lee S. Cohen
Assistant Examiner—Scott M. Getzow
Attorney, Agent, or Firm—John L. Rooney

[57] ABSTRACT

An apparatus and technique for electrical stimulation of the central or peripheral nervous system based upon changes in position of the patient. A position sensor may be chronically implanted in the patient. One preferred mode uses a mercury switch position sensor which indicates whether a patient is erect or supine. This position information is used by a chronically implanted pulse generator to vary the stimulation intensity. The intensity may be controlled by changes in pulse amplitude, pulse width, number of pulses per second, burst frequency, number of pulses per burst, electrode polarity, or any other convenient parameter which accomplishes the particular medical purpose within an application. The output of the chronically implanted pulse generator is applied to the spinal cord, peripheral nerves, and/or targets in the brain with leads and electrodes in a manner consistent with the given medical need. Such stimulation is useful in the treatment of chronic intractable pain, hemodynamic insufficiency resulting in angina, peripheral vascular disease, cerebral vascular disease, various movement disorders, and bowel and bladder control.

5 Claims, 5 Drawing Sheets

POSITION-RESPONSIVE NEURO STIMULATOR

CROSS REFERENCE TO CO-PENDING APPLICATIONS

This application is related to Ser. No. 7/437,265, filed Jan. 31, 1990, entitled "Intravascular Pressure Posture Detector", assigned to the assignee of the present invention.

BACKGROUND OF THE INVENTION

1. Field of the Invention

The present invention relates generally to implantable medical devices and more particularly relates to implantable medical devices for stimulation of the central and peripheral nervous systems.

2. Description of the Prior Art

Chronically implantable stimulators for the brain and spinal cord have been in use for some time. Originally these were used to treat chronic intractable pain. Clinically favorable results were reported in a number of publications including "Long Term Follow Up of Dorsal Cord Stimulation for Chronic Pain Syndrome After Multiple Lumbar Operations", Applied Neurophysiology, Volume 45, pages 201-204, 1982 by J. Siegfried and Y. Lazorthes and "Spinal Epidural Neurostimulation for Treatment of Acute and Chronic Intractable Pain: Initial and Long Term Results", Neurosurgery, Volume 5, pages 344-348, 1979, by R. R. Richardson, et al.

Subsequently, additional medical applications were reported including treatment of peripheral vascular disease as seen in "Spinal Cord Stimulation in Peripheral Vascular Disease" Proceedings on Functional Electrostimulation, 1983, by E. H. Sedgwick, L. S. Illis, and R. C. Tallis. Research continues in the possible treatment of angina and other disorders by spinal cord stimulation.

The earliest practical spinal cord stimulators were passive devices which picked up RF energy transmitted across the skin and applied it via electrodes implanted near the spinal cord. Many medical applications are yet best approached with such a device. The PISCES ® family of spinal cord stimulation systems made available to the medical community by Medtronic, Inc. of Minneapolis, Minn., assignee of the present invention, are examples of passive spinal cord stimulation systems.

A later development in neurological stimulation is the chronically implantable active stimulation system. These consist of a battery operated pulse generator which is electrically coupled to the spinal cord by insulated leads coupled to electrodes normally implanted in the epidural space. The Medtronic ® Itrel ® implantable neurostimulator is an example of an active device. The Itrel II ® implantable pulse generator manufactured Medtronic, Inc. has advanced programmable features permitting mode changes by transcutaneous RF telemetry. These mode changes include modifying the stimulation intensity.

Clinical results have been reported that suggest it is appropriate to lower the stimulation intensity whenever a patient is recumbent. The lower stimulation intensity is adequate for medical efficacy of the treated condition in the supine patient and undesirable side effects are reduced. See "Electrical Stimulation of the Spinal Cord. The Phenomenon of Changing Paresthesias", by G. H. Spincemaille and C. H. A. Wittens. Similarly, increasing intensity is preferred in the erect patient to achieve optimal effectiveness of stimulation.

SUMMARY OF THE INVENTION

The present invention employs a position sensor which can be located in a chronically implanted programmable spinal cord stimulator. The position sensor determines when the patient is in a erect position. This causes the spinal cord stimulator to provide stimulation signals appropriately preprogrammed for the erect position. Whenever the patient reclines, the position sensor notifies the implanted spinal cord stimulator to continue stimulation at new parameters preprogrammed appropriately for the supine position.

Intensity reduction is one form of parameter change appropriate for the supine position. The intensity reduction can take the form of one or a combination of reduced stimulation amplitude, pulse width, pulses per second, decreased burst frequency, or decreased number of pulses per burst. The reduced intensity of stimulation is selected to be sufficient to accomplish the desired medical purpose but with decreased side effects.

The position sensor can employ a number of techniques. The preferred mode uses a mercury switch having a small amount of mercury enclosed within a sealed capsule. Electrical contacts within the sealed capsule may be electrically coupled by the mercury whenever the sensor is in a given attitude. The sensor may be located within an implantable pulse generator or in a separate package, which is either implanted or external.

The output of the implantable pulse generator is coupled to the spinal cord by insulated electrical leads which terminate in electrodes implanted in the epidural space. The implantable pulse generator is programmed by medical personnel via a transcutaneous RF telemetry signal.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
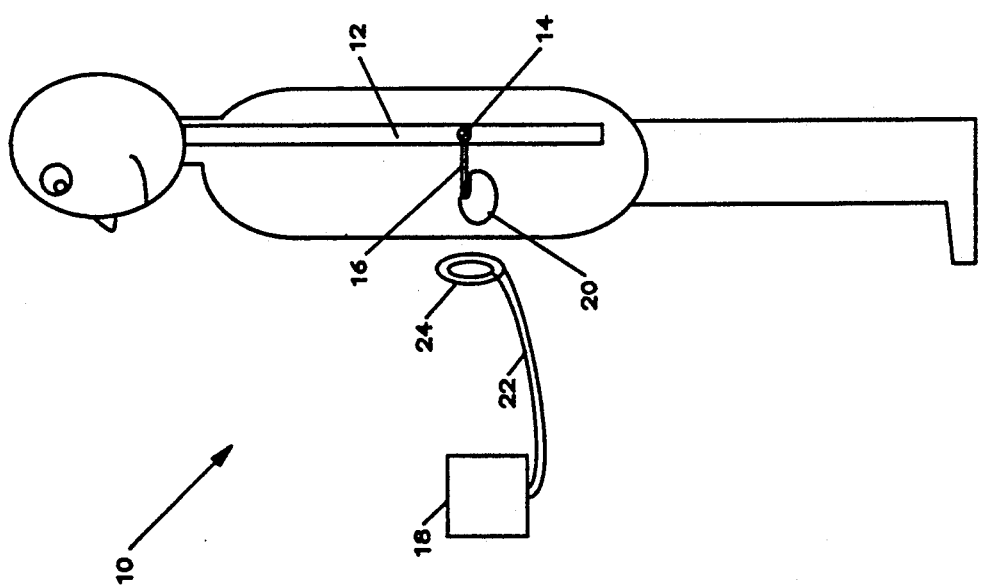
FIG. 1 is a schematic view of a patient with a chronically implanted neurological stimulation system according to the present invention.

FIG. 1 is a schematic view of a patient 10 having a chronically implanted neurological stimulator employing the present invention. Electrode 14 is implanted in the epidural space surrounding the spinal cord 12 as explained in more detail below. Implantable pulse generator 20, containing a position sensor (not shown) is electrically coupled to electrode 14 by insulated lead 16.

Implantable pulse generator has a number of programmable parameters which may be selected noninvasively by programmer 18 communicating through cable 22 to radio frequency antenna 24. Implantable pulse generator 20 is preferably the same as the Itrel II ® neurological implantable pulse generator available to medical personnel through Medtronic, Inc. of Minneapolis, Minn. with the addition of a position sensor as described in detail below.

Figure 2:
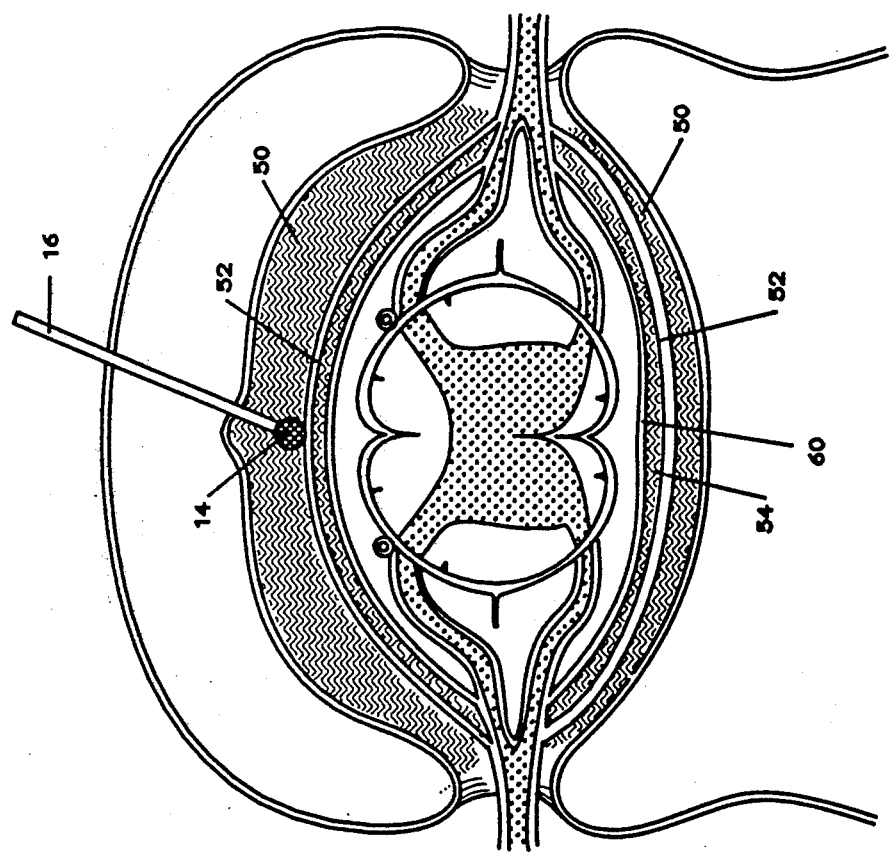
FIG. 2 is a cross sectional view of the spinal column of a patient showing implantation of a stimulation electrode.

FIG. 2 is a cross sectional view of the spinal cord and adjacent tissue of patient 10. Electrode 14 is shown implanted in epidural space 50. Insulated lead 16 is electrically coupled to electrode 14. Shown for purposes of orientation is the subdural space 54 located between dura mater 52 and arachnoid membrane 60.

Figure 3:
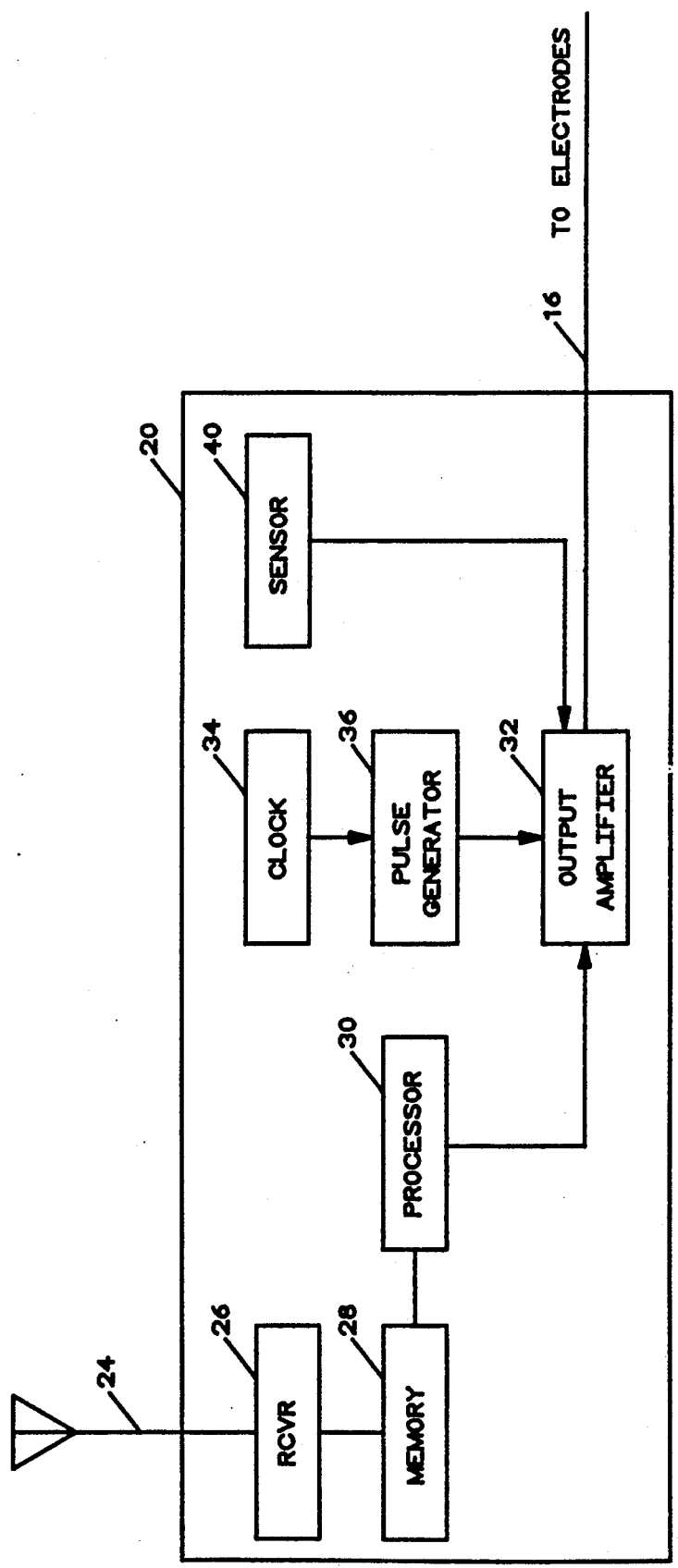
FIG. 3 is a block diagram of an implantable pulse generator employing the present invention.

FIG. 3 is a block diagram of implantable pulse generator 20. As stated above, implantable pulse generator 20 is preferably a Medtronic ® Itrel II ® neurological pulse generator with the modifications as specified. Implantable pulse generator 20 has an internal crystal clock 34 coupled to pulse generator 36 which determines the pulse rate and the number of pulses per burst. The output of pulse generator 36 is amplified by output amplifier 32 to produce the actual stimulation pulse train which is electrically coupled to insulated lead 16.

Programmable parameters are modified in accordance with transcutaneous RF telemetry information received by antenna 24. Receiver 26 decodes the telemetry information which is stored in memory 28. Processor 30 uses the stored parameter information to modify the gain of output amplifier 32.

Sensor 40 is preferably located within the same physical housing as implantable generator. Although a number of embodiments are suitable, the preferred mode employs, by way of example and not to be construed as limiting of the present invention, a mercury switch which is used to sense whether the patient is erect or recumbent.

Figure 4:
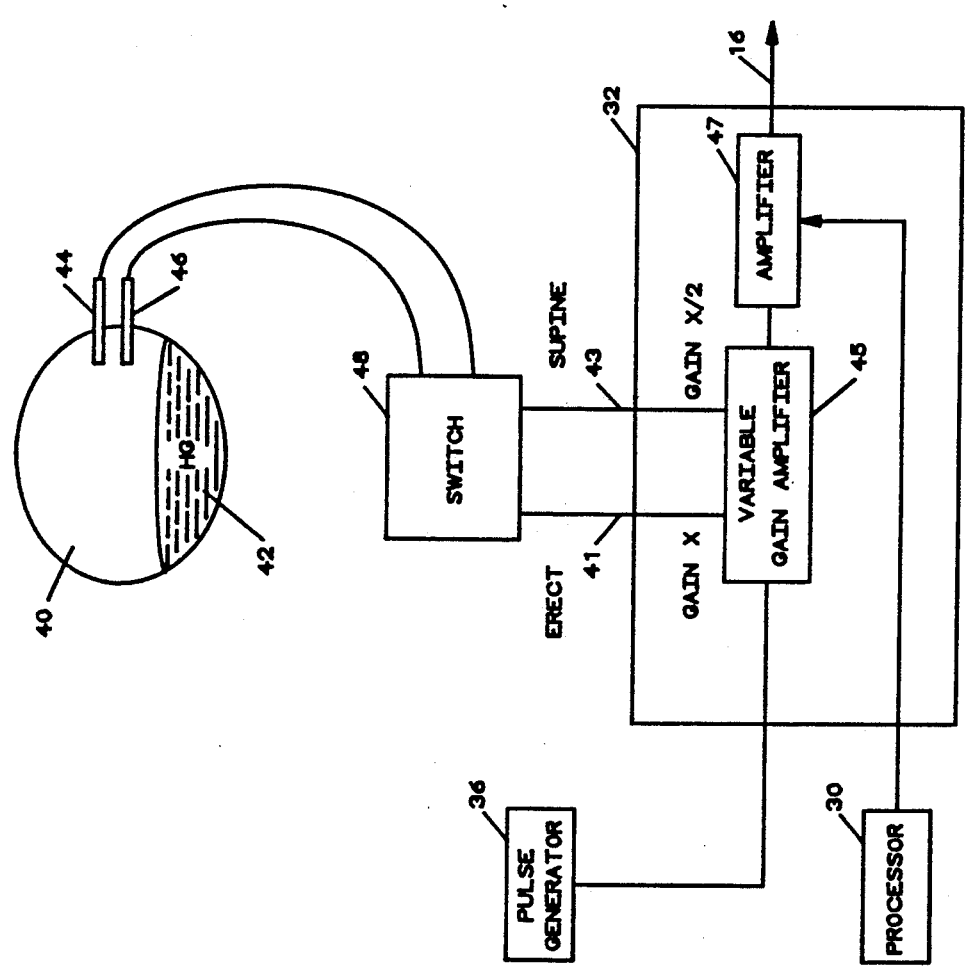
FIG. 4 is a block diagram of the position sensor of a preferred mode of the present invention.

FIG. 4 is a detailed diagram showing the circuitry associated with sensor 40. Sensor 40 is shown with patient 10 in a supine position. It is important that the position of implantable pulse generator 20 be as indicated at the time of implant. This ensures that mercury 42 within sensor 40 does not establish electrical contact between wires 44 and 46 whether patient 10 lies face up, face down, or on either side.

Wires 44 and 46 are coupled to switch 48 as shown. Switch 48 is a semiconductor device which outputs a logical high on line 41 whenever patient 10 is erect (i.e. whenever mercury 42 establishes electrical contact between wires 44 and 46). Similarly, switch 48 outputs a logical high on line 43 whenever patient 10 is supine (i.e. whenever mercury 42 does not establish electrical contact between wires 44 and 46).

Output amplifier 32 receives the outputs of switch 48 permitting it to change output amplitudes. For clarity, only that portion of output amplifier 32 involved in the automatic change of amplitude with patient position is shown. In the preferred mode, the stimulation amplitude is changed upon change of position, although changes to other parameters are also suitable including change of rate and change of number of pulses per burst.

Output amplifier 32 has a stage shown as variable gain amplifier 45. Whenever the patient is erect as indicated by switch 48, variable gain amplifier 45 amplifies the output of pulse generator 36. Whenever the patient is supine, variable gain amplifier is switched to a gain of ½ or such other convenient fraction as is appropriate. Gain of amplifier 47 is adjusted by the output of processor 30 in known fashion.

As explained above, the remaining circuitry of output amplifier 32 is not shown for clarity. However, the output of amplifier 47 is transmitted as the actual stimulation pulse train (see also FIG. 3).

Figure 5:
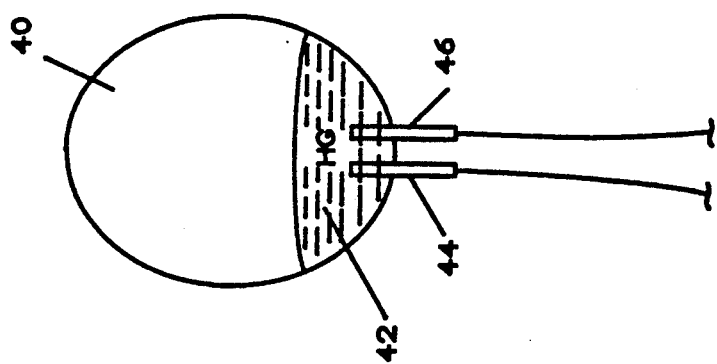
FIG. 5 is a closeup view of the mercury switch of the position sensor.

FIG. 5 is a view of sensor 40 when patient 10 is erect. Notice that in this position, mercury 42 establishes electrical contact between wires 44 and 46. As stated above, the implanting medical personnel must be cautioned that implantable pulse generator 20 must be implanted in the proper attitude within patient 10 to permit sensor 40 to sense the position of patient 10. In some applications, this may prove inconvenient. Therefore, a sensor technique which does not have this limitation may be used. Co-pending patent application entitled "Intravascular Pressure Posture Detector" Ser. No. 07/437,265, filed Jan. 31, 1990, herein incorporated by reference, and assigned to the assignee of the present invention may be employed.

Having thus described the preferred embodiments, those of skill in the art will be readily able to apply the present invention without departing from the scope of the claims which are hereto attached.

What is claimed is:

1. A method of spinal cord stimulation comprising:
   a. sensing the position of a patient and determining whenever said patient is erect and whenever said patient is supine; and,
   b. stimulating the spinal cord of said patient with a series of pulse bursts, and
   c. automatically altering the said spinal cord stimulation in response to said sensing of the position of said patient by lowering the stimulation intensity whenever said patient is supine.

2. A method according to claim 1 wherein said automatically altering step lowers the stimulation intensity by decreasing the frequency of stimulation.

3. A method according to claim 1 wherein said automatically altering step lowers the stimulation intensity by lowering the amplitude.

4. A method according to claim 1 wherein said automatically altering step lowers the stimulation intensity by decreasing the number of pulses per burst.

5. A method according to claim 1 wherein said automatically altering step decreases pulse width.

* * * * *